United States Patent
Asaff Arancibia et al.

(10) Patent No.: US 9,732,024 B2
(45) Date of Patent: Aug. 15, 2017

(54) METHOD TO PURIFY FERULIC ACID AND/OR SALTS THEREOF

(71) Applicant: LABORATORIOS MINKAB, S.A.DEC.V., Tlalnepantla, Estado de Mexico (MX)

(72) Inventors: Jorge Selim Asaff Arancibia, Jalisco (MX); Angel Emilio Aceves Diez, Jalisco (MX); Ruben Herrera Herrera, Jalisco (MX); Maria Lucia Alejo Castillo, Jalisco (MX)

(73) Assignee: LABORATORIOS MINKAB, S.A. de C.V., Estado de Mexico (MX)

( * ) Notice: Subject to any disclaimer, the term of this patent is extended or adjusted under 35 U.S.C. 154(b) by 123 days.

(21) Appl. No.: 14/771,668

(22) PCT Filed: Jul. 24, 2015

(86) PCT No.: PCT/MX2015/000109
§ 371 (c)(1),
(2) Date: Aug. 31, 2015

(87) PCT Pub. No.: WO2017/014621
PCT Pub. Date: Jan. 26, 2017

(65) Prior Publication Data
US 2017/0158595 A1 Jun. 8, 2017

(51) Int. Cl.
*C07C 51/47* (2006.01)
(52) U.S. Cl.
CPC .................................. *C07C 51/47* (2013.01)
(58) Field of Classification Search
None
See application file for complete search history.

(56) References Cited

U.S. PATENT DOCUMENTS

| | | | |
|---|---|---|---|
| 5,288,902 | A | 2/1994 | Taniguchi et al. |
| 6,143,543 | A | 11/2000 | Michelsen et al. |
| 2016/0145183 | A1 | 5/2016 | Revelant et al. |

FOREIGN PATENT DOCUMENTS

| | | |
|---|---|---|
| CN | 1621402 | 6/2005 |
| CN | 101811958 | 8/2010 |

(Continued)

OTHER PUBLICATIONS

Machine English Translation of Torres et al. (WO 2004110975, published Dec. 23, 2004).*

(Continued)

*Primary Examiner* — Sudhakar Katakam
*Assistant Examiner* — Jennifer C Sawyer
(74) *Attorney, Agent, or Firm* — Brooks Kushman P.C.

(57) ABSTRACT

Methods to purify ferulic acid and/or salts thereof, both in solid state as in solution, the methods include: dissolve the ferulic acid, with a selective organic solvent, recover and isolate the solution from the insoluble impurities with filters; recover the organic solvent evaporating the solution; mix the concentrated extract of ferulic acid with water to pre-crystallize the hydrosoluble impurities; evaporate the mixture to remove the remains of the organic solvent; concentrate the mixture free of solvent in an evaporator; cool the mixture down to 40° C.; let the concentrated mixture set for 1 h, to then isolate by sedimentation the water-insoluble impurities; re-heat the mixture free of impurities to 70° C.; purify the mixture through a synthetic resin, transfer the purified mixture to a crystallizing container to crystallize the ferulic acid; remove the mother liquor of crystallization of the precipitate of ferulic acid; dry the ferulic acid.

10 Claims, 1 Drawing Sheet

(56) References Cited

FOREIGN PATENT DOCUMENTS

| | | |
|---|---|---|
| WO | 2004110975 | 12/2004 |
| WO | 2014187784 | 11/2014 |

OTHER PUBLICATIONS

International Search Report for PCT/MX2015/000109, English translation attached to original, Both completed by the Mexican Patent Office on Nov. 16, 2015, All together 5 Pages.

* cited by examiner

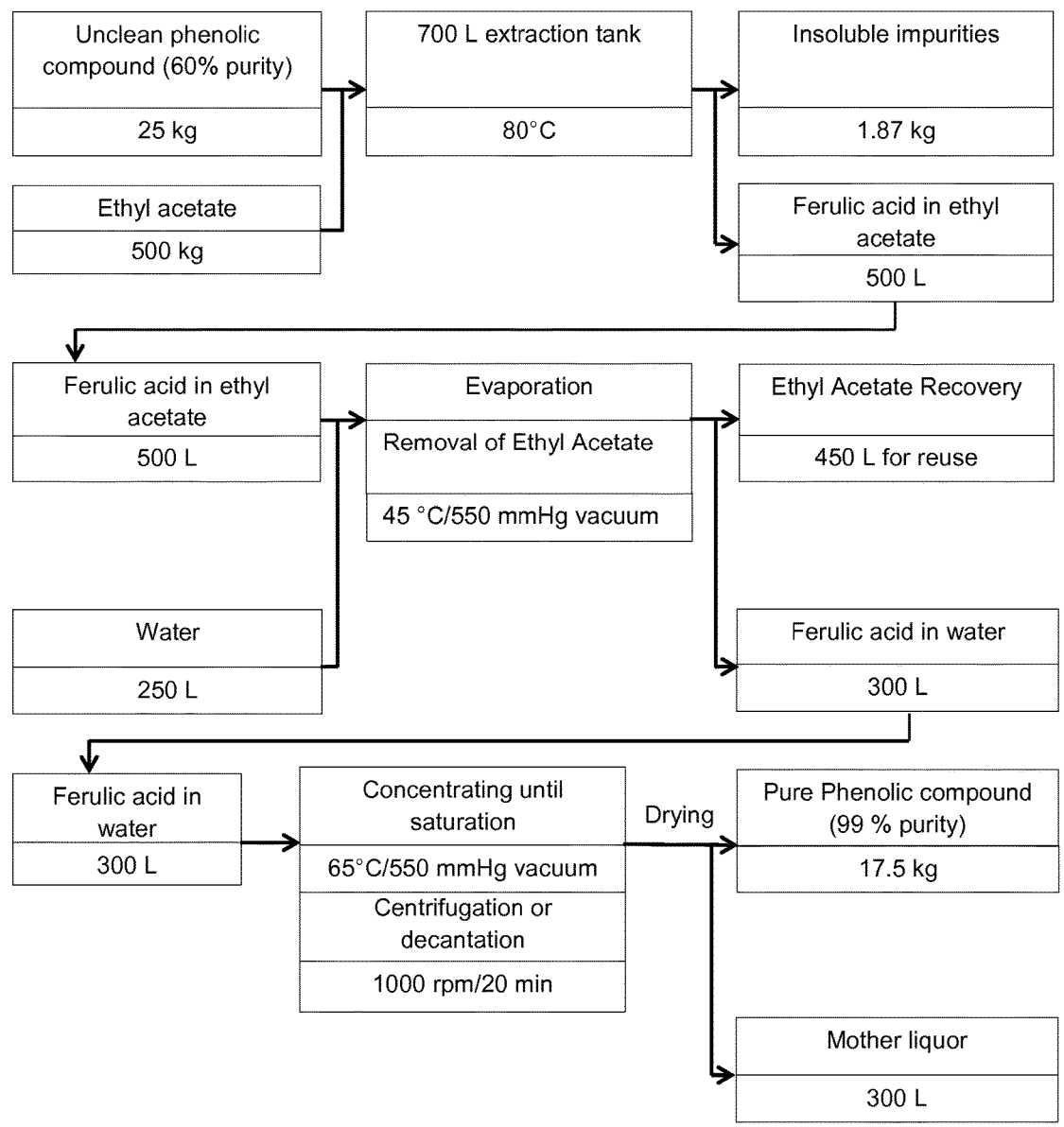

METHOD TO PURIFY FERULIC ACID AND/OR SALTS THEREOF

CROSS-REFERENCE TO RELATED APPLICATION

This application is the U.S. national phase of PCT Application No. PCT/MX2015/000109 filed on Jul. 24, 2015, the disclosure of which is incorporated in its entirety by reference herein.

TECHNICAL FIELD OF THE INVENTION

The present invention is related, preferably, with the technical field of the chemistry, food, cosmetics and pharmaceutical industries; since it provides a method for the purification of ferulic acid and/or salts thereof, and it also provides ferulic acid and/or salts thereof, obtained by said method, which can be useful in the obtention of a product related to the industries of chemistry, food, cosmetology, pharmaceutical, to cite some.

BACKGROUND OF THE INVENTION

Ferulic acid is a very abundant compound in nature, since it is a component of the cell wall of several plant species such as rice, corn, sugar beet and others. However it is not found in its free form, rather it forms glycosidic bonds with the carbohydrate chains in the cell wall, so, for its liberation several hydrolytic methods are used, be it enzymatic or alkaline. For example, in the patent document U.S. Pat. No. 6,143,543 an enzymatic method for the obtention of free ferulic acid is described.

The patent document U.S. Pat. No. 5,288,902 discloses on its example 1, lines 50 to 60, that raw ferulic acid was dissolved in hot water at 90 to 100° C., followed by a cooling, for a re-crystallization, with the purpose of obtaining pure trans-ferulic acid. It is also mentioned that the purity of said ferulic acid is 99.9%. However, one of the inconveniences that this procedure presents is that depending on the origin of the ferulic acid (rice and its derivatives, corn, wheat and other natural sources) other contaminants are found with it, which are also soluble in water like polysaccharides, hemicelluloses, lignins, and by being dissolved in water, they re-crystallize along ferulic acid, and high purity levels are not reached.

Meanwhile, patent application WO2004/110975 discloses a process for the recovery and purification of ferulic acid in its free form using water resulting from corn cooking, known as nejayote, originated from the nixtamal industry. However, according to the purification, it only describes that raw feluric acid can be purified by re-crystallization, gradually decreasing the polarity of a concentrated solution of it in ethyl acetate by the addition of organic solvents of low polarity like methyl chloride and hexane, or by decreasing the pH value of an aqueous alkaline solution.

The patent document CN1621402 refers to the preparation of ferulic acid and the purification process from Chinese medicinal material. The technological process includes the next steps: grind Chinese Ligusticum, angelica or Chuanxiong rhizome, into fine powder; perform a reflux extraction with ethyl ether and solvent methanol, at a pH value of 3-5, to obtain a liquid extract and the recovery of the solvent; wash with dissolvent ethanol and water; filter to obtain a filtrate and recovery of the solvent to obtain a concentrated solution; and dry and freeze in vacuum to obtain the product pure ferulic acid. The obtained product has a purity above 90% and the yield is higher than 65%. The problem with this method is the use of toxic organic solvents, like methanol and ethyl ether, which are not permitted in the food industry, and that remaining may be left in the final product.

The document CN101811958 states a process for the isolation and extraction of natural ferulic acid, with contents higher than 98%, from the residues of processing rice bran oil. The procedure includes the following stages: wash with alcohol; saponify and filter; acidify and filter; dissolve with alcohol and filter; refine with an ionic exchange resin; discolor; concentrate; pump and filter; and drying in vacuum to obtain a white dust with contents of natural ferulic acid higher than 98%. But the inconveniences are: the use of anionic exchange reins, strongly alkaline for purification, in which a loss of product of between 20 and 50% is observed due to the chemical selectivity of them for ferulic acid, which causes retention of the product and cannot be recovered, hence affecting the economics of the process.

Therefore, it is not demonstrated in the state of the technique an efficient methodology for the purification of ferulic acid and/or salts thereof. Reason for which a method to purify ferulic acid and/or salts thereof was developed, which is described next.

OBJECT OF THE INVENTION

An object of the present invention is a method to purify ferulic acid and/or salts thereof, which was extracted by an extraction method with purity inferior to 90% and is in solid state.

Another object of the invention is a method to purify ferulic acid and/or salts thereof, which as extracted by an extraction method with purity inferior to 90%, and is in solution.

One more object of the present invention is ferulic acid and/or salts thereof, purified by any of the purification methods of the present invention.

The invention also has as an object to provide ferulic acid and/or salts thereof, with purity ranging from 98 to 99.9%

BRIEF DESCRIPTION OF FIGURES

FIG. 1 is a flow diagram of a method to purify ferulic acid and/or salts thereof, of the present invention, where ferulic acid and/or salts thereof are in solid state and have a purity of 60%.

DETAILED DESCRIPTION OF THE INVENTION

Some Definitions

With the term ferulic acid, we refer, to ferulic acid itself and also to all of its salts.

With the term pre-crystallization we refer to an initial crystallization of some impurities, before ferulic acid.

The characteristic features of the present invention are clearly shown in the following description, figure and examples that accompany it, which illustrate one of the possible executions of the invention, so by no means, in any way should be considered as a limitant for said invention.

The method to purify ferulic acid and/or salts thereof of the present invention, preferably begins from ferulic acid and/or salts thereof, already extracted by some extraction methods, but said ferulic acid and/or salts thereof have a purity no higher than 90%. Those methods can supply the ferulic acid and/or salts thereof in a solid state or in solution.

When ferulic acid and/or salts thereof are in solid state, the process of the present invention begins with a total dissolution of ferulic acid in stirring tanks, where that dissolution can be performed with a selective organic solvent, for example, ethyl acetate; where the extract that contains ferulic acid and/or salts thereof, is concentrated to its saturation. Then, recovery of the solution and a first elimination of impurities are conducted, with help of filters.

After it, part of the selective solvent is recovered, by subjecting the solution to evaporation and the organic solvent to distillation with equipment that allows its recovery to be reused in other extractions. For example, it can be a vacuum evaporator that allows the recovery of the selective organic solvent, at a temperature from 30 to 60° C., with a vacuum from 400 to 700 Hg mm.

Mix with water the concentrated extract of ferulic acid and/or salts thereof, from the previous stage, in a ratio 1:1, to pre-crystallize the impurities that are water-soluble.

The remaining of the organic solvent are then removed from this mixture, by evaporating it, to a temperature of approximately 60° C.

Once the mixture is free of solvent, it is concentrated in an evaporator at a temperature from 30 to 60° C., with a vacuum from 400 to 700 Hg mm, to half its volume, to later cool it at 40° C. and left to set 1 hour to isolate by sedimentation the insoluble impurities.

The mixture free of insoluble impurities is re-heated at 70° C., to later be applied through a synthetic purification resin, for example PSDVB (polystyrene divinylbenzene resins).

Then, crystallization of ferulic acid and/or salts thereof continues, to which, the resulting mix is transferred to a crystallizing vessel with cooling jacket; where the ferulic acid and/or salts thereof crystallize after 4 hours of being set, at a temperature of 15° C., with a purity of 98 to 99.9%.

Later, extract the precipitate of ferulic acid and/or salts thereof, to then isolate from the mother liquor of crystallization, which can be made by centrifugation. The recovered mother liquor of crystallization, are reused in posterior crystallizations.

Ferulic acid and/or salts thereof, purified, are then dried in a drying equipment with vacuum trays and inert atmosphere for 2 hours, to a humidity inferior to 1%, preferably.

The ferulic acid and/or salts thereof are sieved and packed, in a conventional way.

It is worth mentioning that when ferulic acid and/or salts thereof were extracted and are in solution, it is not required for the method to start with a dissolution with an organic solvent, as it is when the ferulic acid and/or salts thereof are in solid state. This is why that the present invention points out two methods for the purification of ferulic acid and/or salts thereof, depending on its state when purification is started.

This way, with the methods described before, ferulic acid and/or salts thereof is obtained with a purity from 98 to 99.9%; which is covered by the scope of the present invention.

The ferulic acid and/or salts thereof can be used for an endless number of products such as food, cosmetics, medicines and others. This is a reason why these products that contain ferulic acid and/or salts thereof, obtained by the present method, are also included in the protection of the present invention.

EXAMPLE

The following example illustrates one of the preferred modalities of execution of the present invention, supported by FIG. 1.

Example 1. Purification of Ferulic Acid and/or Salts Thereof, from Ferulic Acid and/or Salts Thereof Already Extracted in Solid State In a stirred tank of 700 L, 25 kg of ferulic acid and/or salts thereof were dissolved, which had a purity of 60%, for which 500 L of ethyl acetated were used to achieve a total dissolution of ferulic acid and/or salts thereof. The solution was recovered and the insoluble impurities were isolated with the help of filters, and were subjected to evaporation in a vacuum evaporator that allowed recovery of ethyl acetate, at a temperature of between 30 and 60° C., with a vacuum of between 400 and 700 Hg mm. the recovered ethyl acetate is reused in other extractions.

The concentrated extract of ferulic acid and/or salts thereof was 250 L in volume and was mixed with 250 L of water, to pre-crystallize the soluble impurities in water. For this purpose, the mixture was subject to evaporation to remove the remains of the organic solvent, at a temperature of 60° C.

Once the mixture was free from solvent, it was concentrated in an evaporator to a final volume of 200 L, and after it was cooled to 40° C. and left to set for one hour to isolate by sedimentation the insoluble impurities in water.

The mixture free from impurities was re-heated at 70° C. to be transferred through the synthetic purification resin, PSDVB (polystyrene divinylbenzene resins).

Subsequently, the mixture free of impurities was transferred to a crystallizer container with cooling jacket; where ferulic acid and/or salts thereof crystallized after 4 h of being left to set at a temperature of 15° C., with a purity of 98%.

The mother liquor of crystallization was removed from the precipitate of ferulic acid and/or salts thereof, through centrifugation at 1000 rpm, for 20 minutes. The recovered mother liquor of crystallization was reused in posterior crystallizations.

The ferulic acid and/or salts thereof, already purified, were dried in a drying equipment with vacuum trays and inert atmosphere for 2 h, until a humidity inferior to 1% was achieved.

The obtained ferulic acid and/or salts thereof had a purity of 98% and 17.5 kg of it were recovered, obtaining a global yield of the process of 70%.

The ferulic acid and/or salts thereof were sieved and packed in a conventional way.

The invention claimed is:

1. A Method to purify ferulic acid and/or salts thereof, where the ferulic acid and/or salts thereof are extracted by a method of extraction, with purity less than to 90% and in solid state; wherein said method comprises:
   dissolving ferulic acid and/or salts thereof totally, with a selective organic solvent;
   recovering and separate the solution from water insoluble impurities with the help of filters;
   recovering the selective organic solvent by subjecting the solution to evaporation in a vacuum evaporator that allows the recovery of the selective organic solvent at a temperature between 30 and 60° C., with a vacuum between 400 to 700 Hg mm;

mixing with water the concentrated extract of ferulic acid and/or salts thereof, from the previous step, in a ratio of 1:1, to pre-crystallize the impurities soluble in water;

evaporating the mixture to remove the remains of organic solvent, at a temperature of 60° C., approximately;

concentrating the mixture free of solvent in an evaporator, at 30 to 60° C., with 400 to 700 Hg mm to obtain a final volume of about 40 to 50%;

cooling the concentrated mixture at 40° C., approximately;

letting the concentrated mixture to set, around 1 h, to isolate by sedimentation the water-insoluble impurities;

re-heating the mixture free from impurities at 70° C.;

purifying the re-heated mixture through a synthetic purification resin;

transferring the purified mixture to a crystallizing container with cooling jacket, where the ferulic acid and/or salts thereof crystallize after 4 h of being set, at a temperature of 15° C., with purity from 98 to 99.9%;

removing the mother liquor of crystallization from the precipitate of ferulic acid and/or salts thereof, through centrifugation at 1000 rpm for 20 min; and drying the ferulic acid and/or salts thereof, to be purified, in a drying apparatus having vacuum trays and an inert atmosphere, for 2 h, to obtain humidity less than 1%.

2. The method of claim 1, further comprising sieving of ferulic acid and/or salts thereof.

3. The method of claim 1, wherein the selective organic solvent is ethyl acetate.

4. The method according to claim 1, wherein the purification resin is a polystyrene divinylbenzene resin.

5. The method according to claim 1, wherein said method has a recovery of ferulic acid and/or salts thereof of around 70%.

6. A method to purify ferulic acid and/or salts thereof, wherein ferulic acid and/or salts thereof was extracted by a method of extraction, with a purity less than 90% and is in solution, wherein it includes:

recovering and separate the solution of the insoluble impurities with help of filters;

recovering the ethyl acetate by subjecting the solution to evaporation in a vacuum evaporator that allows the recovery of the selective organic solvent, at a temperature from 30 to 60° C., with a vacuum from 400 to 700 Hg mm;

mixing with water the concentrated extract of ferulic acid and/or salts thereof, from the previous step, in a ratio of 1:1, to pre-crystallize the impurities insoluble in water;

evaporating the mixture to remove the remains of organic solvent, at a temperature of 60° C., approximately;

concentrating the mixture free from solvent in an evaporator from 30 to 60° C., at 400 to 700 Hg mm, to a final volume of 40 to 50%;

cooling the concentrated mixture at 40° C., approximately;

letting the concentrated mixture to set, for around 1 h, to isolate by sedimentation the impurities insoluble in water;

reheating the mixture free from impurities to 70° C.;

purifying the re-heated mixture with the use of a synthetic purification resin;

transferring the purified mixture to a crystallizing container with cooling jacket, where the ferulic acid and/or salts thereof, crystallize after 4 hours of being left to set at a temperature of 15° C., with purity from 98 to 99.9%;

removing the mother liquor of crystallization of the precipitate of ferulic acid and/or salts thereof, through centrifugation at 1000 rpm, for 20 min; and drying the purified ferulic acid and/or salts thereof, in a drying equipment with vacuum trays and inert atmosphere, for 2 h, to a humidity less than 1%.

7. The method of claim 1, further comprising sieving the dried ferulic acid and/or salts thereof.

8. The method of claim 5, wherein the selective organic solvent is ethyl acetate.

9. The method according to claim 5, wherein the purification resin is a polystyrene divinylbenzene resin.

10. The method according to claim 6, wherein the recovery of ferulic acid and/or salts thereof, is at least 70%.

\* \* \* \* \*